(12) United States Patent
Ron

(10) Patent No.: US 8,198,237 B2
(45) Date of Patent: Jun. 12, 2012

(54) CONCENTRATED PROTEIN PREPARATIONS OF BONE MORPHOGENETIC PROTEINS AND METHODS OF USE THEREOF

(75) Inventor: Niles Ron, Framingham, MA (US)

(73) Assignee: Stryker Corporation, Kalamazoo, MI (US)

( * ) Notice: Subject to any disclaimer, the term of this patent is extended or adjusted under 35 U.S.C. 154(b) by 52 days.

(21) Appl. No.: 12/595,171

(22) PCT Filed: May 14, 2008

(86) PCT No.: PCT/US2008/006144
§ 371 (c)(1),
(2), (4) Date: Oct. 8, 2009

(87) PCT Pub. No.: WO2008/143867
PCT Pub. Date: Nov. 27, 2008

(65) Prior Publication Data
US 2010/0144631 A1    Jun. 10, 2010

Related U.S. Application Data

(60) Provisional application No. 60/930,219, filed on May 15, 2007.

(51) Int. Cl.
*A61K 38/17* (2006.01)
*A61K 38/18* (2006.01)
*A61K 38/19* (2006.01)
(52) U.S. Cl. ........ 514/8.8; 514/8.9; 514/16.7; 514/16.8; 514/16.9; 514/17.1
(58) Field of Classification Search ........................ None
See application file for complete search history.

(56) References Cited

U.S. PATENT DOCUMENTS

| 5,385,887 | A | 1/1995 | Yim et al. |
| 6,875,432 | B2 * | 4/2005 | Liu et al. .................... 424/130.1 |
| 6,994,883 | B2 * | 2/2006 | Layrolle et al. .............. 427/2.27 |
| 2003/0105004 | A1 * | 6/2003 | Jones et al. ..................... 514/12 |
| 2005/0170070 | A1 * | 8/2005 | Layrolle et al. ................ 427/2.1 |
| 2006/0286289 | A1 * | 12/2006 | Prajapati et al. ............. 427/2.31 |
| 2008/0234727 | A1 | 9/2008 | Garigapati et al. |

FOREIGN PATENT DOCUMENTS

| WO | 93/00050 | 1/1993 |
| WO | 97/31661 | 9/1997 |

OTHER PUBLICATIONS

Written Opinion for PCT/US2008/006144 dated Aug. 5, 2008 (7 pages).
International Search Report for PCT/US2008/006144 dated Aug. 5, 2008 (3 pages).
* cited by examiner

*Primary Examiner* — Elizabeth C Kemmerer
(74) *Attorney, Agent, or Firm* — K&L Gates LLP

(57) ABSTRACT

Disclosed herein are heretofore undescribed preparations of highly concentrated, solubilized proteins, such as but not limited to, Bone Morphogenetic Proteins. Such protein preparations can be formulated in an aqueous carrier at protein concentrations in excess of 10 mg/ml when using the methods of manufacture taught herein. Such methods yield stable protein preparations in either solubilized or lyophilized form. The protein preparations of the present invention are particularly beneficial when administered either locally or systemically, in part, because low administration volumes can be accomplished. This is especially important for local treatment of certain anatomic locations such as, for example, the synovial fluid of a joint when treating osteoarthritis with BMP-7 or the intradiscal space when treating degenerative disc disease with BMP-7.

10 Claims, 1 Drawing Sheet

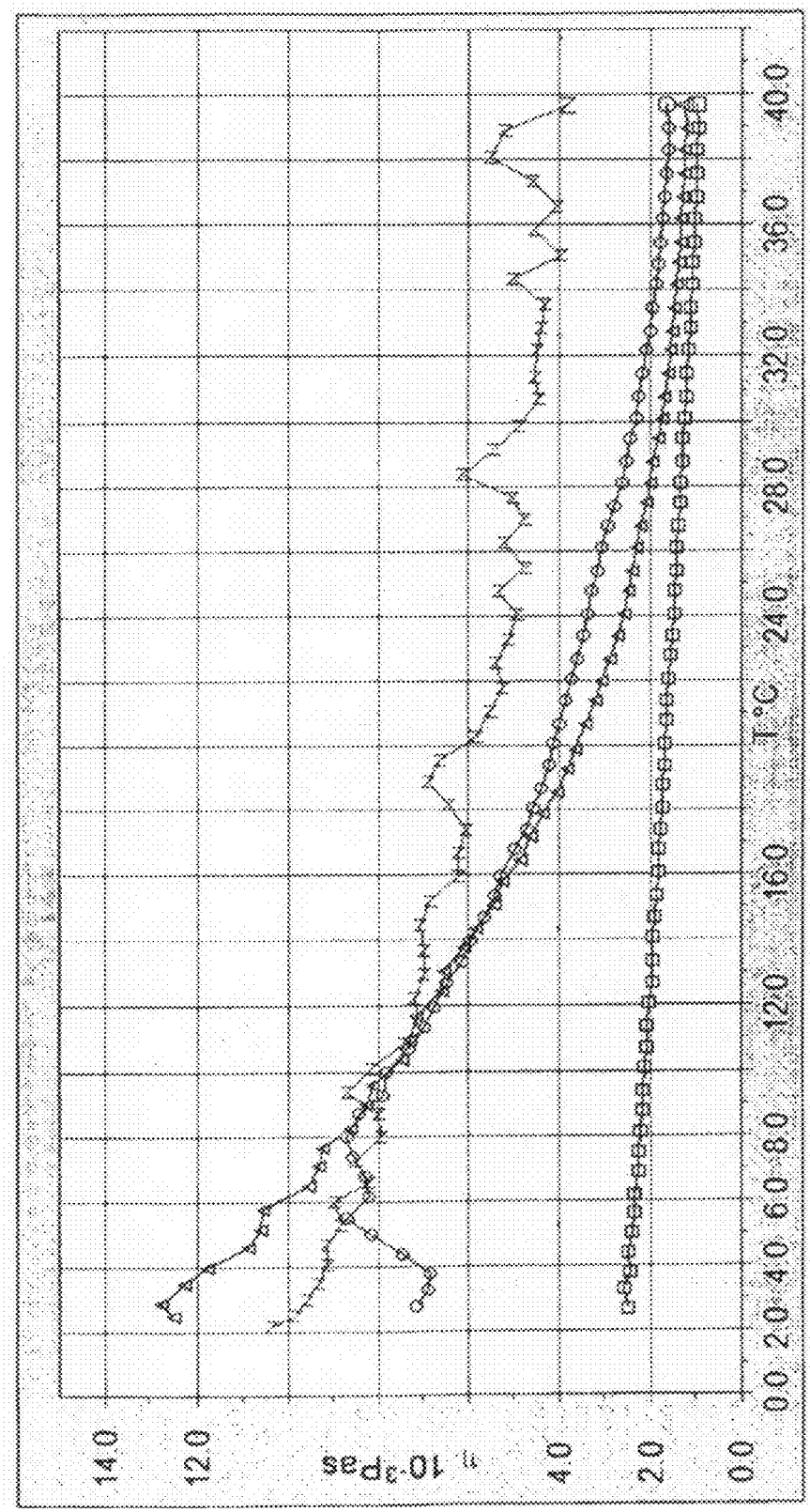

CONCENTRATED PROTEIN PREPARATIONS OF BONE MORPHOGENETIC PROTEINS AND METHODS OF USE THEREOF

CROSS-REFERENCE TO RELATED APPLICATIONS

This application is the U.S. national phase application of International Patent Application No. PCT/US08/06144, filed May 14, 2008, which claims priority to and the benefit of U.S. Provisional Patent Application No. 60/930,219, filed on May 15, 2007, the contents of which are incorporated by reference herein.

FIELD OF THE INVENTION

The invention relates to heretofore undescribed preparations of highly concentrated, aqueous preparations of proteins typically insoluble at physiological conditions (for example, physiological pH and ionic strength). More specifically, the invention relates to highly concentrated protein preparations of Bone Morphogenetic Proteins and their therapeutic uses.

BACKGROUND

Protein-based therapeutics have proven highly effective for a variety of disorders, injuries and diseases. Apart from the performance challenges associated with protein-based therapeutics, numerous other types of challenges arise during the development of such therapeutics, including protein processing considerations such as ease and cost of manufacturing, stability and shelf-life, as well as modes of administration, dosages and form of effective dosage, to name but a few.

Certain therapeutically significant proteins are particularly difficult because of their inherent insolubility under physiological conditions, such as but not limited to physiological pH. This insolubility is exacerbated when highly concentrated aqueous solutions are desirable. One class of proteins which is inherently insoluble under physiological conditions is the TGF-beta superfamily of cysteine knot proteins. A similarly behaving subfamily includes the Bone Morphogenetic Proteins (BMPs), for example, BMP-2, BMP-7 (also known as OP-1), GDF-5 (also known as CDMP-1 and MP-52), GDF-6 (also known as BMP-13 and CDMP-2).

It is an object of the present invention to provide highly concentrated aqueous protein preparations of such proteins, including but not limited to, BMPs. It is a further object to provide methods of treatment of skeletal and non-skeletal disorders, injuries and diseases using such preparations.

SUMMARY OF THE INVENTION

The present invention is based on the discovery that heretofore undescribed aqueous preparations of proteins which are highly concentrated, i.e., at least about two- to about five-fold, preferably about three-fold, more concentrated than those known in the art, can be readily accomplished using the methods and reagents disclosed herein. Briefly, aqueous protein solutions of at least about 4 mg/ml, can be accomplished using a specified combination of ionic strength, pH and buffering systems; and, this solubility matrix of specific solubilization conditions results in highly efficient manufacture of such protein preparations with a high rate of recovery. Of particular significance, the present invention's highly concentrated protein preparations permit the clinician to administer locally or systemically effective doses of proteins in minimal administration volumes, thereby allowing administration to physiologically-constrained sites such as intrajoint or intra-intervertebral disc sites.

In one aspect, the invention is an aqueous preparation of Bone Morphogenetic Protein (BMP) at high concentrations. As contemplated herein below, other similar proteins can be used in the preparations of the present invention. In a preferred embodiment, the protein preparation comprises an aqueous carrier and bone morphogenetic protein solubilized in said carrier at a concentration of at least about 10 mg/ml. Certain preferred embodiments have a protein concentration greater than about 20 mg/ml; greater than about 25 mg/ml; greater than about 30 mg/ml; and, greater than about 40 mg/ml. In certain embodiments, the protein concentration is in the range of about 10 to 60 mg/ml.

In one preferred protein preparation, the aqueous carrier has an ionic strength of at least about 10 mM. In another, the aqueous carrier has an ionic strength of no more than about 100 mM. In yet another, the aqueous carrier has an ionic strength of no more than about 10 mM; no more than about 20 mM; and, no more than about 50 mM.

Certain preferred embodiments of the protein preparation of the present invention comprise an aqueous carrier having a pH of at least about 2. Others have a pH of no more than about 5. More preferred embodiments have a pH of about 3. In certain embodiments, the pH is in the range from about 2 to about 5.

In accordance with the present invention, a preferred protein preparation has a protein concentration of about 20-60 mg/ml; an ionic strength of about 0-50 mM; and a pH of about 2.5-4. A more preferred preparation comprises the protein described herein as BMP-7 in a concentration of more than 20 mg/ml; an ionic strength of about 10 mM; and a pH of about 3.5.

Regarding each of the foregoing embodiments, the protein preparation is solubilized at a temperature of about 25° C. The protein preparations of the present invention are preferably homogeneous solutions, i.e., preferably the solutions contain no protein precipitate.

In yet other embodiments, the protein preparations further comprise a stabilizing excipient, such as but not limited to excipients selected from the group consisting of: sugars, polyols, surfactants, and any combination thereof. In certain other embodiments, the protein preparations comprise an aqueous carrier which is a buffer of the single acidic group type selected from the group consisting of: potassium phosphate, proprionic acid, lactic acid, trifluoroacetic acid and acetic acid; or the two acidic group type selected from the group consisting of: sodium glutamate and sodium succinate. As contemplated herein, the preparations of the present invention can be lyophilized or can be a reconstituted lyophilate.

More generally, a protein suitable for use in the high concentration preparations of the present invention can be mono- or dimeric; can have a molecular weight of about 25-50 kd; and can have a pI range of about 5-10. Generally, proteins which are most suitable are hydrophobic proteins having poor solubility under physiological conditions, such as but not limited to physiological pH.

As described in detail elsewhere herein, certain preferred protein preparations can comprise a protein known as a cysteine knot protein. Exemplary cysteine knot proteins include PDGF, VEGF and NGF. In other preferred embodiments, the protein preparations comprise a member of the TGF-beta superfamily of proteins. In more preferred embodiments, the protein preparations comprise a member of the BMP subfamily of the TGF-beta superfamily of proteins. Particularly preferred BMPS include one or more of BMP-2, BMP-4, BMP-5, BMP-6, BMP-7, GDF-5, GDF-6 GDF-7, further including sequence variants of any one of the foregoing. Variants contemplated herein include but are not limited to a protein having at least about 50% amino acid sequence identity with a member of the BMP subfamily within the conserved C-terminal cysteine-rich domain. More particularly preferred BMPs are BMP-2, GDF-5, GDF-6 and GDF-7. Most particularly preferred is BMP-7.

In another aspect, the present invention provides methods of treating disorders, injuries and diseases of skeletal and non-skeletal tissues. For example, one preferred method of treating a skeletal tissue disorder, injury or disease comprises the step of administering to a subject in need thereof any one of the aforementioned protein preparations, wherein said protein preparation is in a dose effective to treat said skeletal tissue disorder, injury or disease. In certain preferred methods, the skeletal tissue is mineralized; in others it is non-mineralized skeletal tissue.

Preferred embodiments can effectively treat a skeletal tissue disorder, injury or disease selected from the group consisting of metabolic bone disease, osteoarthritis, osteochondral disease, rheumatoid arthritis, osteoporosis, bone fractures, Paget's disease, periodontitis, and dentinogenesis. Other preferred embodiments can effectively treat a non-mineralized skeletal tissue disorder, injury or disease selected from the group consisting of osteoarthritis, osteochondral disease or defect, chondral disease or defect, rheumatoid arthritis, trauma-induced and inflammation-induced cartilage degeneration, age-related cartilage degeneration, articular cartilage injuries and diseases, full thickness cartilage defects, superficial cartilage defects, sequelae of systemic lupus erythematosis, sequelae of scleroderma, periodontal tissue regeneration, hierniation and rupture of intervertebral discs, degenerative diseases of the intervertebral disc (for example, degenerative disc disease), osteocondrosis, and injuries and diseases of ligament, tendon, synovial capsule, synovial membrane and meniscal tissues.

Certain other preferred embodiments can effectively treat tissue injury selected from the group consisting of: trauma-induced and inflammation-induced cartilage degeneration, articular cartilage injuries, full thickness cartilage defects, superficial cartilage defects, hierniation and rupture of inter-vertebral discs, degeneration of intervertebral discs due to an injury(s); and injuries of ligament, tendon, synovial capsule, synovial membrane and meniscal tissues.

In another embodiment, the invention provides a method of treating a non-skeletal tissue, comprising the step of administering to a subject in need thereof one or more of the foregoing protein preparations, wherein said protein preparation is in a dose effective to treat said non-skeletal tissue disorder, injury or disease. Such a method is effective to treat a disorder, injury or disease of a non-skeletal tissue selected from the group consisting of: liver disease, liver resection, hepatectomy, renal disease, chronic renal failure, central nervous system ischemia or trauma, neuropathy, motor neuron injury, dendritic cell deficiencies and abnormalities, Parkinson's disease, ophthalmic disease, ocular scarring, retinal scarring, ulcerative diseases of the gastrointestinal tract, fibrosis, fibrotic disorders, scleroderma, and pulmonary fibrosis.

A most preferred disease for treatment in accordance with the present invention is osteoarthritis. In osteoarthritis and other disorders, injuries or diseases of joint tissues, an effective dose of a protein preparation can be administered to the synovial space such as but not limited to that of a knee, hip or articulating joint. In one preferred embodiment, the protein preparation is administered via direct injection into the synovial space.

Another most preferred disease for treatment in accordance with the present invention is degenerative disc disease, also referred to herein as IVD disease. In the case of this disease, an effective dose can be administered to the intradiscal space, for example, via direct injection into the nucleus pulposus or annulus fibrosus.

Generally, the methods of the present invention involve an administering step wherein the administration can be local or systemic. In a preferred method, an effective dose of protein is about 1 mg to 30 mg in about 100 microliters to 3 ml. A more preferred method uses a preparation of protein selected from the group consisting of: BMP-2, BMP-4, BMP-5, BMP-6, BMP-7, GDF-5, GDF-6 GDF-7, and sequence variants of any one of the foregoing. A most preferred method uses a preparation of BMP-7.

In other embodiments, the present methods can be performed pre- or post-surgery. In certain other embodiments, the administering step can be performed more than once.

In other embodiments of the present invention, the above-described methods further comprise a step of admixing said protein preparation with a suitable matrix material prior to administration. In yet other embodiments, the above-described methods further comprise a step of coating an implantable medical device with one or more of the previously described protein preparations.

In yet another aspect, the present invention contemplates a kit comprising a lyophilized bone morphogenetic protein and a reconstitution diluent, wherein the protein and the diluent are in separate containers, and wherein the amounts of diluent an protein are sufficient only for preparation of solubilized protein at a concentration of at least about 10 mg/ml. In certain embodiments, the kit further comprises a matrix. In others, the kit further comprise an implantable device suitable for coating with the protein.

In a further aspect, the invention provides a kit for the treatment of a disorder, injury or disease (such as but not limited to those disorders, injuries and/or diseases described elsewhere herein) which comprises a lyophilized protein, preferably a bone morphogenetic protein, and a reconstitution diluent. In a preferred embodiment, the protein and the diluent are in separate containers and further the kit comprises a plurality of separate containers each containing an amount of diluent, such that the amounts of diluent in a kit are sufficient to prepare solubilized protein preparations ranging in concentration from at least about 2 mg/ml to about 60 mg/ml for use in the treatment of a disorder, injury or disease. In a further embodiment, the concentration and volume of solubilized protein preparations are customized for treatment of the particular target disorder, injury or disease.

In another aspect, the present invention provides a method for manufacturing a concentrated form of lyophilized recombinant bone morphogenetic protein comprising the steps of: (1) providing a processing solution of recombinant bone morphogenetic protein, the weight per volume of protein in said processing solution being less than the weight per volume specified for lyophilization; (2) adjusting the weight per volume of protein in said processing solution to produce a lyophilization solution, the weight per volume of protein in said lyophilization solution being greater than that of the processing solution; (3) filling a vial suitable for lyophilization with a specified volume of said lyophilization solution; and, (4) lyophilizing said lyophilization solution to manufacture a concentrated form of lyophilized recombinant bone morphogenetic protein. In a related embodiment, the method further comprises the step of reconstituting said lyophilized recombinant bone morphogenetic protein in a reconstitution diluent wherein the volume of diluent is the same as the volume in step 3 identified above. In another related embodiment, the method further comprises the step of reconstituting said lyophilized recombinant bone morphogenetic protein in a reconstitution diluent wherein the volume of diluent is less than the volume in step 3 identified above. In certain preferred embodiments of the kit, the concentrated form is achieved post-processing and contains solubilized bone morphogenetic protein in a concentration of at least 10 mg/ml. In a most preferred embodiment, a kit comprises a concentrated form of recombinant bone morphogenetic protein prepared according to the method set forth immediately above.

In yet another aspect, the present invention provides a method for preparing a concentrated form of bone morphogenetic protein comprising the steps of:
(1) providing a processing solution of bone morphogenetic protein, the weight per volume of protein in said processing solution being the same as the weight per volume specified for lyophilization;
(2) filling a vial suitable for lyophilization with a specified volume of said processing solution thereby producing a lyophilization solution;
(3) lyophilizing said lyophilization solution; and,
(4) packaging the lyophilized lyophilization solution together with a specified volume of reconstitution diluent, the volume of said diluent being less than the specified fill volume of step 3.

In one preferred embodiment of this method, the method further comprises the step of adjusting the weight per volume of protein in the processing solution to produce an adjusted lyophilization solution, the weight per volume of protein in said adjusted lyophilization solution being greater than that of the processing solution.

In yet another aspect, the present invention provides a method for preparing a concentrated form of protein in lyophilized or other reconstitutible non-liquid form comprising the steps of:
(1) providing a processing solution of protein, the weight per volume of protein in said processing solution being the same as the weight per volume specified for lyophilization or other reconsitutible non-liquid form;
(2) providing a vial suitable for lyophilization (or other form) for containing a specified volume of said processing solution thereby producing a lyophilization (or other form) solution;
wherein the weight per volume of protein in each of the processing and lyophilization (or other form) solution is at least 2 mg/ml.

In a preferred embodiment, this method can further comprise the step of providing a lyophilized form of the lyophilization solution or a reconstitutible form of the other non-liquid form. In another preferred embodiment, the method can further comprise the step of providing a specified volume of diluent for rehydrating the lyophilized form or reconstituting the other reconstitutible non-liquid form, the volume of said diluent being sufficient to permit preparation of an aqueous protein preparation having at least 2 mg/ml; or further comprising the step of providing instructions for rehydrating the lyophilized form or reconstituting the other reconstitutible non-liquid form so as to product an aqueous protein preparation having at least 2 mg/ml.

The present invention contemplates that a protein preparation prepared in accordance with any one of the methods described herein can be used to treat a disorder, injury or disease such as but not limited to those disorders, injuries and/or diseases described elsewhere herein.

FIGURES

FIG. 1 illustrates certain exemplary aqueous protein preparations in accordance with the present invention.

DETAILED DESCRIPTION

The present invention is based on the discovery that heretofore undescribed aqueous preparations of proteins which are highly concentrated, i.e., at least about two- to about five-fold, preferably about three-fold, more concentrated than those known in the art, can be readily accomplished using the methods and materials disclosed herein. Briefly, aqueous protein solutions of at least about 4 mg/ml, can be accomplished using a specified combination of ionic strength, pH and buffering systems; and, this solubility matrix of specific solubilization conditions results in highly efficient manufacture of such protein preparations with a high rate of recovery. Of particular significance, the present invention's highly concentrated protein preparations permit the clinician to administer locally or systemically effective doses of proteins in minimal administration volumes, thereby allowing administration to physiologically-constrained sites such as intrajoint or intra-intervertebral disc sites.

Protein Preparation Considerations

In certain preferred embodiments of the present invention, protein concentrations range from about 10 mg/ml to about 60 mg/ml. In certain other preferred embodiments, the protein concentration is at least about 4 mg/ml but not more than about 100 mg/ml. A particularly preferred range is about 20 to about 40 mg/ml. A more preferred range is about 10 to about 30 mg/ml. A most preferred range is about 5 to about 30 mg/ml. In a currently most preferred embodiment, the concentration is at least about 10 mg/ml. A most preferred concentration is about 15 mg/ml. In an even more currently preferred embodiment, the concentration is about 20 mg/ml. In another, it is greater than about 20 mg/ml. In yet another, it is greater than about 25 mg/ml. In the case of BMP-7, a most preferred concentration range is about 10 to about 40 mg/ml and a most preferred concentration is about 20 mg/ml. Preferably, no protein precipitate is observed in any of the foregoing protein preparations of the present invention when held at room temperature (about 25° C.). And, the foregoing protein preparations are stable in solubilized forms as well as lyophilized forms when prepared and formulated in accordance with the teachings set forth herein.

In certain preferred embodiments of the above-described protein preparations, ionic strength ranges from at least about 10 mM to no more than about 100 mM. In certain other preferred embodiments, ionic strength is at least about 20 mM but not more than about 50 mM. A particularly preferred range is about 25 mM to about 40 mM. A more preferred range is about 10 mM to about 20 mM. A most preferred range is about 0 to about 20 mM. In a currently most preferred embodiment, the ionic strength is about 10 mM. In an even more currently preferred embodiment, the ionic strength is about 5 mM. A most preferred ionic strength is about 0 mM. In the case of BMP-7, a most preferred range is about 0 to about 50 mM and a most preferred ionic strength is about 10 mM. Preferably, no precipitate is observed in any of the foregoing protein preparations when held at room temperature (about 25° C.).

In one preferred protein preparation, the aqueous carrier has an ionic strength of at least about 10 mM. In another, the aqueous carrier has an ionic strength of in the range of 0 to about 100 mM. In yet another, the aqueous carrier has an ionic strength from 0 to about 10 mM; from 0 to about 20 mM; and, from 0 to about 50 mM.

In certain preferred embodiments of the above-described protein preparations, preferred pH ranges are from at least about 2 to no more than about 5. In certain other preferred embodiments, pH is at least about 2 but not more than about 4. A particularly preferred range is about 3 to about 4. A more preferred range is about 2.5 to about 3.5. A most preferred range is about 2.5 to about 4. In a currently most preferred embodiment, the pH is about 2.5. In an even more currently preferred embodiment, the pH is about 3. A most preferred pH is about 3.5. In the case of BMP-7, a most preferred pH range is about 2.4 to about 4 and a most preferred pH is about 3.5. No precipitate is observed in any of the foregoing protein preparations when held at temperatures ranging from about 4° C. to about 25° C.

In certain preferred embodiments of the above-described protein preparations, preferred pI ranges are from at least about 5 to no more than about 10. In certain other preferred embodiments, pI is at least about 7 but not more than about 9. A particularly preferred range is about 6.5 to about 9. A more preferred range is about 7.5 to about 8.5. A most preferred range is about 6.5 to about 10. In an even more currently preferred embodiment, the pI is about 6.5 to about 9. In the case of BMP-7, a most preferred pI range is about 6.5 to about 9 and a most preferred pI is about 9. Preferably, no proetin precipitate is observed in any of the foregoing protein preparations when held at room temperature (about 25° C.).

The protein preparations of the present invention can be formulated using acid buffers. Specifically, single acidic buffers as well as double acidic buffers can be used successfully. The aqueous carrier comprises a buffer of the single acidic group type selected from the group consisting of: potassium phosphate, proprionic acid, lactic acid, trifloroacetic acid and acetic acid; or the two acidic group type selected from the group consisting of: sodium glutamate and sodium succinate. More preferred acids include lactic acid, TFA, potassium phosphate. Lactic acid is most preferred. Other acids, such as citric acid, ascorbic acid, and sodium phosphate can also be readily employed when practicing the present invention.

Certain embodiments of the protein preparations of the present invention further comprise a stabilizing excipient selected from the group consisting of sugars, polyols and surfactants. Glucose, sucrose, raffinose, trehalose, lactose are among the preferred sugars. Lactose is preferred. Trehalose is most preferred. Manitol and sorbitol are among the preferred polyols. Manitol is most preferred. Preferable concentrations of sugars or polyols range from about 0% to 10%; most preferably 2.5% to 10%. Tween 80, Tween 20, and Pluronic F-68 are among the preferred non-ionic surfactants useful as stabilizing excipients. Tween 80 and Tween 20 are most preferred. Concentrations of these surfactants range from about 0.01% to about 0.1%. Generally, the range of non-ionic surfactant concentrations useful herein is about 0.005% to about 10%. Combinations of any one or more of the foregoing stabilizing excipients are contemplated herein.

Bone Morphogenetic Proteins (BMPs) and Other Preferred Proteins

The present invention contemplates useful and preferred proteins to have one or more of the following features: The protein is mono- or dimeric. The protein is basic. The protein exhibits a pI of about 5 to about 10; preferably about 6 to about 9 or about 5 to about 7 or about 7.5 to about 9. The protein has a molecular weight of about 25 kd to about 50 kd. The protein is hydrophobic. The protein is insoluble under physiological conditions, especially at concentrations in excess of about 4 mg/ml. The present invention contemplates one such type of preferred proteins known as cysteine knot proteins (See, McDonald et al., *A Structural Superfamily of Growth Factors Containing a Cystine Knot Motif*, Cell 73: 421-424 (1993)). The present invention further contemplates another more preferred type of such proteins known as the TGF-beta superfamily of proteins. And, the present invention further contemplates another most preferred type of such proteins known as the Bone Morphogenetic Proteins (BMPs).

As stated above, BMPs are a preferred exemplary protein for purposes of the present invention. BMPs belong to the TGF-β superfamily. The TGF-β superfamily proteins are cytokines characterized by six-conserved cysteine residues. The human genome contains about 42 open reading frames encoding TGF-β superfamily proteins. The TGF-β subfamily includes, but is not limited to, TGFs (e.g., TGF-β1, TGF-β2, and TGF-β3), activins (e.g., activin A) and inhibins, macrophage inhibitory cytokine-1 (MIC-1), Mullerian inhibiting substance, anti-Mullerian hormone, and filial cell line derived neurotrophic factor (GDNF). Structurally, such proteins are homo or heterodimers expressed as large precursor polypeptide chains containing a hydrophobic signal sequence, an N-terminal pro region of several hundred amino acids, and a mature domain comprising a variable N-terminal region and a highly conserved C-terminal region containing approximately 100 amino acids with a characteristic cysteine motif having a conserved six or seven cysteine skeleton. These structurally-related proteins have been identified as being involved in a variety of developmental events. As used herein, "TGF-β subfamily," "TGF-βs," "TGF-β ligands" and grammatical equivalents thereof refer to the TGF-β subfamily members, unless specifically indicated otherwise.

The TGF-β superfamily proteins can at least be divided into the BMP subfamily and the TGF-β subfamily based on sequence similarity and the specific signaling pathways that they activate. The BMP subfamily includes, but is not limited to, BMP-2, BMP-3 (osteogenin), BMP-3b (GDF-10), BMP-4 (BMP-2b), BMP-5, BMP-6, BMP-7 (OP-1, osteogenic protein-1), BMP-8 (OP-2), BMP-8B (OP-3), BMP-9 (GDF-2), BMP-10, BMP-11 (GDF-11), BMP-12 (GDF-7), BMP-13 (GDF-6, CDMP-2), BMP-15 (GDF-9), BMP-16, GDF-1, GDF-3, GDF-5 (CDMP-1, MP-52), and GDF-8 (myostatin). For purposes of the present invention, preferred superfamily proteins include BMP-2, -4, -5, -6 and -7 and GDF-5, -6, and -7, as well as MP-52. Particularly preferred proteins include BMP-2, BMP-7 and GDF-5, -6, and -7. A most preferred exemplary BMP is BMP-7. Preferred BMPs can have a six- or seven-cysteine conserved region in their C-terminal region. BMPs are also present in other animal species. Furthermore, there is allelic variation in BMP sequences among different members of the human population, and there is species variation among BMPs discovered and characterized to date. As used herein, "BMP subfamily," "BMPs," "BMP ligands" and grammatical equivalents thereof refer to the BMP subfamily members, unless specifically indicated otherwise.

The TGF-β superfamily is in turn a subset of the cysteine knot cytokine superfamily. Additional members of the cysteine knot cytokine superfamily include, but are not limited to, platelet derived growth factor (PDGF), vascular endothelial growth factor (VEGF), placenta growth factor (PlGF), noggin, neurotrophins (BDNF, NT3, NT4, and βNGF), gonadotropin, follitropin, lutropin, interleukin-17, and coagulogen.

Publications describing certain of these preferred proteins, as well as their chemical and physical properties, include: BMP-7 and OP-2 (U.S. Pat. No. 5,011,691; U.S. Pat. No.

5,266,683; Ozkaynak et al., EMBO J., 9, pp. 2085-2093 (1990); OP-3 (WO94/10203 (PCT US93/10520)), BMP-2, BMP-4, (WO88/00205; Wozney et al. Science, 242, pp. 1528-1534 (1988)), BMP-5 and BMP-6, (Celeste et al., PNAS, 87, 9843-9847 (1991)), Vgr-1 (Lyons et al., PNAS, 86, pp. 4554-4558 (1989)); DPP (Padgett et al. Nature, 325, pp. 81-84 (1987)); Vg-1 (Weeks, Cell, 51, pp. 861-867 (1987)); BMP-9 (WO95/33830 (PCT/US95/07084); BMP-10 (WO94/26893 (PCT/US94/05290); BMP-11 (WO94/26892 (PCT/US94/05288); BMP-12 (WO95/16035 (PCT/US94/14030); BMP-13 (WO95/16035 (PCT/US94/14030); GDF-1 (WO92/00382 (PCT/US91/04096) and Lee et al. PNAS, 88, pp. 4250-4254 (1991); GDF-8 (WO94/21681 (PCT/US94/03019); GDF-9 (WO94/15966 (PCT/US94/00685); GDF-10 (WO95/10539 (PCT/US94/11440); GDF-11 (WO96/01845 (PCT/US95/08543); BMP-15 (WO96/36710 (PCT/US96/06540); MP-121 (WO96/01316 (PCT/EP95/02552); GDF-5 (CDMP-1, MP52) (WO94/15949 (PCT/US94/00657) and WO96/14335 (PCT/US94/12814) and WO93/16099 (PCT/EP93/00350)); GDF-6 (CDMP-2, BMP13) (WO95/01801 (PCT/US94/07762) and WO96/14335 and WO95/10635 (PCT/US94/14030)); GDF-7 (CDMP-3, BMP12) (WO95/10802 (PCT/US94/07799) and WO95/10635 (PCT/US94/14030)) The above publications are incorporated herein by reference.

The term "morphogenic protein" refers to a protein belonging to the TGF-β superfamily of proteins which has true morphogenic activity. For instance, such a protein is capable of inducing progenitor cells to proliferate and/or to initiate a cascade of events in a differentiation pathway that leads to the formation of cartilage, bone, tendon, ligament, neural or other types of differentiated tissue, depending on local environmental cues. Thus, morphogenic proteins useful in this invention can behave differently in different surroundings. In certain embodiments, a morphogenic protein of this invention can be a homodimer species or a heterodimer species. The term "osteogenic protein (OP)" refers to a morphogenic protein that is also capable of inducing a progenitor cell to form cartilage and/or bone. The bone can be intramembranous bone or endochondral bone. Most osteogenic proteins are members of the BMP subfamily and are thus also BMPs. However, the converse can not be true. According to this invention, a BMP identified by DNA sequence homology or amino acid sequence identity must also have demonstrable osteogenic or chondrogenic activity in a functional bioassay to be an osteogenic protein. Appropriate bioassays are well known in the art; a particularly useful bioassay is the heterotopic bone formation assay (see, U.S. Pat. No. 5,011,691; U.S. Pat. No. 5,266,683, for example).

Structurally, BMPs are dimeric cysteine knot proteins. Each BMP monomer comprises multiple intramolecular disulfide bonds. An additional intermolecular disulfide bond mediates dimerization in most BMPs. BMPs may form homodimers. Some BMPs may form heterodimers. BMPs are expressed as pro-proteins comprising a long pro-domain, one or more cleavage sites, and a mature domain. The pro-domain is believed to aid in the correct folding and processing of BMPs. Furthermore, in some but not all BMPs, the pro-domain may noncovalently bind the mature domain and may act as an inhibitor (e.g., Thies et al. (2001) Growth Factors 18:251-259).

BMPs are naturally expressed as pro-proteins comprising a long pro-domain, one or more cleavage sites, and a mature domain. This pro-protein is then processed by the cellular machinery to yield a dimeric mature BMP molecule. The pro-domain is believed to aid in the correct folding and processing of BMPs. Furthermore, in some but not all BMPs, the pro-domain may noncovalently bind the mature domain and may act as a chaperone, as well as an inhibitor (e.g., Thies et. Al. (2001) Growth Factors, 18:251-259).

As further contemplated herein, the term "BMP" refers to a protein belonging to the BMP subfamily of the TGF-β superfamily of proteins defined on the basis of DNA homology and amino acid sequence identity. According to this invention, a protein belongs to the BMP subfamily when it has at least 50% amino acid sequence identity with a known BMP subfamily member within the conserved C-terminal cysteine-rich domain that characterizes the BMP subfamily. Members of the BMP subfamily can have less than 50% DNA or amino acid sequence identity overall. As used herein, the term "BMP" also embraces proteins which are amino acid sequence variants, domain-swapped variants, and/o truncations and active fragments of naturally occurring bone morphogenetic proteins, as well as heterodimeric proteins formed from two different monomeric BMP peptides, such as BMP-2/7; BMP-4/7: BMP-2/6; BMP-2/5; BMP-4/7; BMP-4/5; and BMP-4/6 heterodimers. Suitable BMP variants and heterodimers include those set forth in US 2006/0235204; WO 05/097825; WO 00/020607; WO 00/020591; WO 00/020449; WO 05/113585; WO 95/016034 and WO93/009229.

As contemplated herein, useful BMPs include those containing sequences, which are homologues or variants, that share at least 50%, preferably at least 60%, more preferably at least 70% and most preferably at least 85%, amino acid sequence identity with the C-terminal cysteine domain of BMP-2, BMP4, BMP-5, BMP-6, BMP-7, GDF-5, GDF-6, or GDF-7. As contemplated herein, preferred BMPs include biologically active variants of any such BMPs, including variants containing conservative amino acid substitutions. All that is required by the present invention is that these variants retain biological activity comparable to the native form. As used herein, the term "BMP related protein" or "BMP related proteins" means any one or all of the foregoing proteins.

Proteins useful herein also include any known naturally occurring native proteins exhibiting one or more of the above-identified preferable features, including allelic, phylogenetic counterparts and other variants thereof which exhibit one or more of the aforementioned properties. Variants include forms having varying glycosylation patterns, varying N-termini, and active truncated or mutated forms of a native protein. Useful proteins also include those that are biosynthetically produced (e.g., "muteins" or "mutant proteins"). Moreover, the proteins contemplated herein include biologically active variants of any of the above-listed proteins, including variants containing conservative amino acid changes as described elsewhere herein; and osteogenically active proteins having the conserved seven-cysteine skeleton or domain as defined below. For instance, useful osteogenic proteins also include those containing sequences that share at least 70% amino acid sequence homology with the C-terminal seven-cysteine domain of BMP-7. To determine the percent homology of a candidate amino acid sequence to that seven-cysteine domain, the candidate sequence and the sequence of the domain are aligned. The alignment can be made with, e.g., the dynamic programming algorithm described in Needleman et al., J. Mol. Biol. 48:443 (1970), and the Align Program, a commercial software package produced by DNAstar, Inc. The teachings by both sources are incorporated by reference herein. An initial alignment can be refined by comparison to a multi-sequence alignment of a family of related proteins. Once the alignment between the candidate sequence and the seven-cysteine domain is made and refined, a percent homology score is calculated. The aligned amino acid residues of the two sequences are compared sequentially for their similarity to each other. Similarity factors include similar size, shape and electrical charge. One particularly preferred method of determining amino acid similarities is the PAM250 matrix described in Dayhoff et al., Atlas of Protein Sequence and Structure 5:345-352 (1978 & Supp.), herein incorporated by reference. A similarity score is first calculated as the sum of the aligned pairwise amino acid similarity scores. Insertions and deletions are ignored for the purposes of percent homology and identity. Accordingly, gap penalties are not used in this calculation. The raw score is then normalized by dividing it by the geometric mean of the scores of the candidate sequence and the seven-cysteine domain. The geometric mean is the square root of the product of these scores. The normalized raw score is the percent homology.

Furthermore, other useful proteins also include those containing sequences that share greater than 60% identity with the seven-cysteine domain of the BMP subfamily. In certain preferred embodiments, useful osteogenic proteins include those having an amino acid sequence sharing at least 70% (e.g., at least 80%) sequence homology or "similarity" with all or part of a naturally occurring reference morphogenic protein. A preferred reference protein is human BMP-7. Other known osteogenic proteins can also be used as a reference sequence. In one embodiment, a candidate amino acid sequence can be aligned with a reference amino acid sequence by using the method of Needleman et al., J. Mol. Biol. 48:443-453 (1970), implemented conveniently by computer programs such as the Align program (DNAstar, Inc.). Internal gaps and amino acid insertions in the candidate sequence are ignored for purposes of calculating the level of homology or identity between the candidate and reference sequences. "Amino acid sequence homology" is understood herein to include both amino acid sequence identity and similarity. Homologous sequences share identical and/or similar amino acid residues, where similar residues are conservative substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence. Certain particularly preferred morphogenic polypeptides share at least 60% (e.g., at least 65%) amino acid sequence identity with the C-terminal seven-cysteine domain of human BMP-7.

As used herein, "conservative substitutions" are residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al. (1978), 5 Atlas of Protein Sequence and Structure, Suppl. 3, Ch. 22, pp. 354-352, Natl. Biomed. Res. Found., Washington, D.C. 20007. Examples of conservative substitutions are substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine. The term "conservative variant" or "conservative variation" also includes the use of a substituting amino acid residue in place of an amino acid residue in a given parent amino acid sequence, where antibodies specific for the parent sequence are also specific for, i.e., "cross-react" or "imuno-react" with, the resulting substituted polypeptide sequence.

Manufacture of Concentrated Protein Preparations: General Considerations

The methods of the present invention increase ease of protein processing during manufacturing, while reducing in-process product losses and yielding a high quality, final desired high concentration protein preparation of the present invention. Such preparations evidence higher recoveries, reduced aggregation and permit improved fill-level accuracy as compared with art-recognized methods routinely employed by scientists and process engineers.

An exemplary method follows which describes processing (preparation, fill, lyophilization, and finish operations) a preferred protein, BMP-7, at low concentrations ($\leq 20$ mg/mL), while yielding a product that can be reconstituted to a desired target higher protein concentration (20 to 40 mg/mL). This methodology of the present invention allows execution of all manufacturing operations at a lower protein concentration—this increases ease of processing as the viscosity of the solution handled is lower and it also reduces in-process losses during manufacturing (since a fixed volume lost contains a lower mass of protein due to the lower concentration used during processing). The lower concentration used during processing also allows for the product to be stored and processed at refrigerated temperatures (2 to 8° C.), without resulting in a dramatic increase in viscosity as would otherwise be observed if high protein concentrations were used during processing.

Usually drug products are processed and filled at the same concentration as the final desired target. For example, if the target protein concentration for administration is 40 mg/mL, the protein preparation (in the presence of appropriate stabilizing excipients) would typically be filled at 40 mg/mL and the freeze-dried product reconstituted with the same volume of diluent as the fill volume prior to lyophilization (freeze-drying).

In the methodology disclosed herein, a different approach is used. For example, if it is desired to have 1 mL of protein solution at 40 mg/mL for administration, the processing (upstream manufacturing) would be conducted at a lower concentration, say 20 mg/mL. The fill would be 2 mL at 20 mg/mL, and the product would be reconstituted with 1 mL reconstitution diluent following freeze-drying. Hence, the manufacturing (processing) operations are conducted at a lower concentration than the final target yielding the following benefits: (a) this increases ease of processing as the viscosity of the solution handled is lower, (b) it also reduces in-process losses during manufacturing (since a fixed volume lost contains a lower mass of protein due to the lower concentration used during processing), (c) the lower concentration used during processing also allows for the in-process intermediates to be stored (and/or processed) at refrigerated temperatures (2 to 8° C.), without resulting in a dramatic increase in viscosity as would otherwise be observed if high protein concentrations were used during processing (See FIG. 1).

By way of another example as illustrative of the present invention, if a target volume of V mL is desired at a protein concentration of C mg/mL for administration, the protein preparation/fill/finish operations can be conducted at C/N mg/mL with a fill volume of V*N mL, with final reconstitution of the lyophilized product with V mL reconstitution diluent, where N (N>1) is a suitable scaling factor, which can be appropriately chosen based on the viscosity and processability of the protein solution. Preferably, N equals about 2. A preferred range is N equals about 2 to about 4; another more preferred range is N equals about 2 to about 10.

This methodology allows execution of all manufacturing operations at a lower protein concentration—this increases ease of processing as the viscosity of the solution handled is lower and it also reduces in-process losses during manufacturing (since a fixed volume lost contains a lower mass of protein due to the lower concentration used during processing). The lower concentration used during processing also allows for the product to be stored and processed at refrigerated temperatures (2 to 8° C.), without resulting in a dramatic increase in viscosity as would otherwise be observed if high protein concentrations were used during processing.

In addition, the above advantages also serve to yield a product with higher quality attributes (for example, if processing is done at a lower protein concentration then critical physicochemical protein attributes such as aggregation tend to be lower than if the protein was processed at a higher concentration) and lower cost of goods (lower COGS due to smaller mass loss of protein and a higher quality product, as discussed above).

The above-described protocols have been successfully implemented to manufacture protein preparations ranging from about 10 to about 60 mg/ml. Using a titration matrix of varying ionic strengths, pHs and protein concentrations (mg/ml), it was discovered that highly concentrated preparations of protein in aqueous carriers are possible without risk of precipitation. Generally, as ionic strength is decreased, pH is contemporaneously decreased thereby maintaining a solubilized protein in an aqueous carrier comprising one or more of the buffer systems described elsewhere herein. That is, using a titration matrix in which ionic strength and pH are simultaneously titrated downward, it is possible to achieve conditions suitable for maintaining solubilized protein at heretofore undescribed high concentrations in an aqueous carrier. As described elsewhere, certain preferred combinations of protein concentration, pH and ionic strength using certain preferred buffering systems result in a highly stable, aqueous preparation of concentrated protein unlike anything previously described in the art. Stabilizing excipients can be used optionally as described earlier.

In yet another manufacturing aspect, the present invention also provides a method for preparing a concentrated form of bone morphogenetic protein comprising the steps of:
(1) providing a processing solution of bone morphogenetic protein, the weight per volume of protein in said processing solution being the same as the weight per volume specified for lyophilization;
(2) filling a vial suitable for lyophilization with a specified volume of said processing solution thereby producing a lyophilization solution;
(3) lyophilizing said lyophilization solution; and,
(4) packaging the lyophilized lyophilization solution together with a specified volume of reconstitution diluent, the volume of said diluent being less than the specified fill volume of step 3.

In one preferred embodiment of this method, the method further comprises the step of adjusting the weight per volume of protein in the processing solution to produce an adjusted lyophilization solution, the weight per volume of protein in said adjusted lyophilization solution being greater than that of the processing solution.

In still another manufacturing aspect, the present invention also provides a method for preparing a concentrated form of protein in lyophilized or other reconstitutible non-liquid form comprising the steps of:
(1) providing a processing solution of protein, the weight per volume of protein in said processing solution being the same as the weight per volume specified for lyophilization or other reconstitutible non-liquid form;
(2) providing a vial suitable for lyophilization (or other form) for containing a specified volume of said processing solution thereby producing a lyophilization (or other form) solution;
wherein the weight per volume of protein in each of the processing and lyophilization (or other form) solution is at least 2 mg/ml.

In a preferred embodiment, this method can further comprise the step of providing a lyophilized form of the lyophilization solution or a reconstitutible form of the other non-liquid form. In another preferred embodiment, the method can further comprise the step of providing a specified volume of diluent for rehydrating the lyophilized form or reconstituting the other reconstitutible non-liquid form, the volume of said diluent being sufficient to permit preparation of an aqueous protein preparation having at least 2 mg/ml; or further comprising the step of providing instructions for rehydrating the lyophilized form or reconstituting the other reconstitutible non-liquid form so as to product an aqueous protein preparation having at least 2 mg/ml.

In summary, the present invention contemplates that a protein preparation prepared in accordance with any one of the methods taught herein can be used to treat a disorder, injury or disease such as but not limited to those disorders, injuries and/or diseases described elsewhere herein.

Kits

The present invention also provides kits useful for the treatment of skeletal or non-skeletal tissue disorders, injuries or diseases. The kits are particularly useful for treating joints impacted by disease, especially osteoarthritis and osteochondral disease; and for treating intervertebral discs affected by injury or disease. In a preferred embodiment, the kits of the present invention comprise one or more protein preparations, and one or more reconstitution diluents. Optionally, a kit of the present invention can further comprise one or more additional biologically active agents. In a particularly preferred embodiment, the protein is a BMP. In a still more particularly preferred embodiment, the protein is BMP-7. The kits of the present invention can also comprise a matrix for admixture with the protein for local implantation at a site of injury or disease; or an implantable medical device suitable for coating with the protein prior to implantation. In a further aspect, the invention also provides a kit for the treatment of a disorder, injury or disease (such as but not limited to those disorders, injuries and/or diseases described elsewhere herein) which comprises a lyophilized protein, preferably a bone morphogenetic protein, and a reconstitution diluent. In a preferred embodiment, the protein and the diluent are in separate containers and further the kit comprises a plurality of separate containers each containing an amount of diluent, such that the amounts of diluent in a kit are sufficient to prepare solubilized protein preparations ranging in concentration from at least about 2 mg/ml to about 60 mg/ml for use in the treatment of a disorder, injury or disease. In a further embodiment, the concentration and volume of solubilized protein preparations are customized for treatment of the particular target disorder, injury or disease.

Therapeutic Interventions and Methods of Treatment

In the case of skeletal disorders, a number of factors can cause or contribute to cartilage degeneration in mammals, including trauma and inflammatory disease. Damage to cells resulting from the effects of inflammatory response has been implicated as the cause of reduced cartilage function or loss of cartilage function in diseases of the joints (e.g., rheumatoid arthritis (RA) and osteoarthritis (OA)). In addition, autoimmune diseases such as systemic lupus erythematosis (SLE) and scleroderma can also be characterized by a degradation of connective tissue. In the case of some cartilage degenerative diseases such as osteoarthritis (OA), the mechanisms that turn the normal aging of articular cartilage into the pathological OA process are currently unknown. Each of the foregoing diseases can be effectively treated with the materials and methods of the present invention.

As stated earlier, the BMP preparations of the invention can be used effectively to treat skeletal diseases or injuries. For example, the preparations can be used to treat a bone fracture, such as an open fracture or a closed fracture. For the treatment of a closed fracture, the preparation is preferably injected at the fracture site. For open fractures, critical size defects or persistent nonunions, the preparations can be administered by surgical implantation at the fracture site. In both cases, the preparation can be administered alone, or in combination with a suitable carrier, matrix or scaffold, such as a bone cement, a calcium phosphate material, a gel material or a collagen matrix. Suitable carriers, matrices and scaffolds include those disclosed in U.S. Pat. Nos. 6,919,308; 6,949,251; and 7,041,641.

In a preferred embodiment, the BMP preparations of the invention can be used to treat a disease or injury resulting in cartilage degradation or a cartilage defect. For example, the preparations can be applied to a cartilage defect site, such as a degenerative intervertebral disc, or other fibrocartilaginous tissue, including a tendon, a ligament or a meniscus. Such methods are set out in U.S. Pat. No. 6,958,149. The preparations of the invention can also be used to treat a defect or degeneration of articular cartilage, as set forth in published PCT application WO 05/115438, such as the cartilage lining of a joint, such as a synovial joint, including a knee, an elbow, a hip, or a shoulder. In this embodiment, the preparation is preferably injected into the synovial space of the joint. In another embodiment, the preparations of the invention are used to treat an articular cartilage defect site, such as a chondral defect or an osteochondral defect, in a joint. Such articular cartilage defects can be the result of a disease process, such as osteoarthritis or rheumatoid arthritis, or due to injury of the joint. In this embodiment, the preparation can be injected into the joint space or it can be surgically implanted. For example, the preparation can be placed within the defect either alone or in combination with one or more additional active agents, a supporting matrix or scaffold, or marrow stromal cells. The preparation can, optionally, be covered with a suitable covering, for example a muscle flap or a bioresorbable membrane, such as a collagen membrane.

As will be appreciated by those skilled in the art, the concentration of the compounds described in a therapeutic composition will vary depending upon a number of factors, including without limitation the dosage of the drug to be administered and the route of administration. The preferred dosage of drug to be administered also is likely to depend on variables including, but not limited to, the type and extent of a disease, tissue loss or defect, the overall health status of the particular patient, the relative biological efficacy of the compound selected, the preparation of the compound, the presence and types of excipients in the preparation, and the route of administration. The present invention may be provided to an individual where typical doses range from about 10 ng/kg to about 1 g/kg of body weight per day; with a preferred dose range being from about 0.1 mg/kg to 100 mg/kg of body weight, and with a more particularly preferred dosage range of 10-1000 µg/dose. In a particularly preferred embodiment, a dose of 10-1000 µg of a BMP-7 is administered to an individual afflicted with osteoarthritis.

Cartilage repair and regeneration is one of the major obstacles in current orthopedics. The importance is enormous because cartilage injury and degenerative disorders such as osteoarthritis, intervertebral disc degeneration and meniscal tears are a major cause of disability among the adult population in the United States.

Cartilage is connective tissue composed of chondrocytes embedded in an extracellular matrix of collagen fibers, proteoglycans, and other non-collagenous proteins. There are two forms of cartilage—articular and non-articular. Articular cartilage is a thin layer of connective tissue, which covers the ends of bones in joints. Non-articular cartilage includes fibrocartilage and elastic cartilage and includes intervertebral discs, meniscus, trachea, larynx, nose, ear and ribs.

The function of cartilage is to cushion load bearing, resist wear, and allow for almost frictionless movement of joints. Defects in cartilage tissue, often caused by trauma, abnormal wear or disease, can lead to pain and stiffness, and if left untreated, may progress and ultimately require replacement of the entire joint. For example, articular cartilage defects often lead to early degradation of the articular surface and may eventually result in osteochondral defects, osteoarthritis or both.

Osteoarthritis is considered a process of attempted, but gradually failing, repair of damaged cartilage extracellular matrix, as the balance between synthesis and breakdown of matrix components is disturbed and shifted toward catabolism.

The ability of cartilage tissue to regenerate on its own is severely limited due to its avascular nature. Repair of osteochondral detects; which involves both the cartilage tissue and the underlying bone, occurs to a limited extent promoted by the presence of both stem cells and growth and differentiation factors brought into the defect by the blood and/or marrow. In animal studies, these defects undergo some repair with formation of a new layer of bone and cartilage, but the macromolecular organization and the biochemical characteristics of the cartilage matrix are imperfect. Type I collagen, rather than Type II collagen, and proteoglycans that are not cartilage specific, such as dermatan sulfate containing proteoglycans, make up the repair tissue and result in fibrillations and degenerative changes over time. And, repair of cartilage defects that do not penetrate into the subchondral bone does not occur, even to a limited extent.

Moreover, surgical treatment of cartilage defects is complex and has been demonstrated to have only limited success. For example, articular cartilage defects are treated with an arthroscopic approach where loose bodies are debrided and transition areas are smoothed. However, this method alone frequently does not provide long lasting relief of the symptoms. Knee replacements often require resecting significant amounts of bone and often require multiple surgeries.

The meniscus is a small horseshoe shaped tissue located between the bone ends inside the knee joint, which acts as a shock absorber. There are two menisci in each knee on either side of the knee. They are usually strong in young people and with age become more brittle and tear more easily. Tears are extremely common with anterior cruciate ligament (ACL) injuries. Meniscal fibrocartilage, like articular hyaline cartilage, has a limited capacity to heal, particularly in the middle and inner avascular regions. The current treatment for small tears is to leave them alone if they do not cause much trouble. Surgical options for treating meniscal tears depend on a number of factors including the nature and extent of the injury and most importantly, its location. Tears in the vascularized region, which is integrated with the highly vascularized synovium have been successfully repaired by suturing. Partial or total meniscectomy is the normal surgical treatment for symptomatic tears within the avascular two thirds of the meniscus. Tears in the latter meniscus regions are the most common types seen clinically. Irrespective of whether open, arthroscopic, total or partial meniscectomy are employed, osteoarthritis is a frequent sequela in these patients within a few years post surgery. Therefore, the common form of repair is to only partially remove the torn bits and to repair the cartilage by stapling it. Unfortunately, the healing process following this procedure is slow. Moreover, if the repair is not successful, then the entire torn meniscus must subsequently be removed.

The major cause of persistent and often debilitating back pain is intervertebral disc (IVD) degeneration also known as degenerative disc disease (DDD). As discs degenerate, they cause the adjoining vertebrae to become compressed, often resulting in severe pain.

The IVD as a syndesmosis provides articulation between adjoining vertebral bodies and acts as a weight bearing cushion which dissipates axially applied spinal loads. These biomechanical functions are made possible by the unique structure of the IVD which is composed of an outer collagen-rich annulus fibrosus surrounding a central hydrated proteoglycan rich gelatinous nucleus pulposus. Superior and inferior cartilaginous endplates, thin layers of hyaline-like cartilage covers the interfaces of the vertebral bodies within the disc.

Lumbar disc degeneration represents a substantial social and economic burden to the community which is manifest principally as low back pain (LBP). It is estimated that as much as 80% of the population experience at least one significant episode of LBP during life, and approximately 2.5% of the working population will take some sick leave during the year as a result of LBP. The direct costs of LBP in modern Western countries has been estimated at $9 billion, most of which is spent on consulting general practitioners, physical therapists and other conservative practitioners (Williams D A et al., (1998) Health care and indemnity costs across the natural history of disability in occupational low back pain, Spine 23:2329-36). Total indirect expenditure, including surgical management may be ten times higher (Maetzel and Li (2002) The economic burden of low back pain: a review of studies published between 1996 and 2001, Best Prac Res Clin Rheumatol 16:23-30; Walker et al., (2003) The economic burden, Proceedings of the Spine Society of Australia Annual Scientific Meeting, Canberra, Australia).

Disc degeneration is a natural phenomenon that occurs, in most instances, from the time of skeletal maturity (Vernon-Roberts (1992) Age-related and degenerative pathology of intervertebral discs and apophyseal joints, In: The lumbar spine and back pain. Fourth edition, Jayson M I V, Ed. Churchill Livingstone, Edinburgh, Chapter 2, 17-41). It is consistent with advancing age but in many cases is also associated with pain, particularly in the lumbar spine, and restricted mobility. Symptoms of LBP often resolve spontaneously over time as patients modify their lifestyles to accommodate restricted mobility. In many cases however, it remains a significant factor that requires surgical intervention. The traditional "gold standard" surgical treatment for chronic LBP has been spinal fusion to immobilize the one or more painful level. Fusion is expensive because it requires prolonged hospitalization and specialist surgical expertise, and although most of these patients will experience short-term pain relief there is evidence now that fusion does not provide the best outcome. Long-term studies suggest that spinal fusion actually promotes degeneration at levels adjacent to the fusion site (Lee (1988) Accelerated degeneration of the segment adjacent to a lumbar fusion, Spine 13:375-7.). In the same way that artificial prostheses were developed 50 years ago to restore function to arthritic and fractured hips and knees, prostheses are now being developed with the aim of restoring full mechanical function to discs that have become painful and arthritic due to chronic degeneration (Szpaalski et al (2002) V Spine arthroplasty: a historical review, Eur Spine J 11:S65-S84). It is however too early to know if any of the myriad models undergoing trials will provide long-term benefit.

Additionally, as described below, the protein preparations, preferably the BMP preparations of the present invention can be used to treat diseases or injuries of non-skeletal tissues. As further contemplated by the present invention, BMPs are capable of inducing the developmental cascade of bone morphogenesis and tissue morphogenesis for a variety of tissues in mammals different from bone or bone cartilage. This morphogenic activity includes the ability to induce proliferation and differentiation of progenitor cells, and the ability to support and maintain the differentiated phenotype through the progression of events that results in the formation of bone, cartilage, non-mineralized skeletal or connective tissues, and other adult tissues.

For example, BMPs can be used for treatment to prevent loss of and/or increase bone mass in metabolic bone diseases. General methods for treatment to prevent loss of and/or increase bone mass in metabolic bone diseases using osteogenic proteins are disclosed in U.S. Pat. No. 5,674,844, the disclosures of which are hereby incorporated by reference. BMPs of the present invention can be used for periodontal tissue regeneration. General methods for periodontal tissue regeneration using osteogenic proteins are disclosed in U.S. Pat. No. 5,733,878, the disclosures of which are hereby incorporated by reference. BMPs can be used for liver regeneration. General methods for liver regeneration using osteogenic proteins are disclosed in U.S. Pat. No. 5,849,686, the disclosures of which are hereby incorporated by reference. BMPs can be used for treatment of chronic renal failure. General methods for treatment of chronic renal failure using osteogenic proteins are disclosed in U.S. Pat. No. 6,861,404, the disclosures of which are hereby incorporated by reference. BMPs can be used for enhancing functional recovery following central nervous system ischemia or trauma. General methods for enhancing functional recovery following central nervous system ischemia or trauma using osteogenic proteins are disclosed in U.S. Pat. No. 6,407,060, the disclosures of which are hereby incorporated by reference. BMPs can be used for inducing dendritic growth. General methods for inducing dendritic growth using osteogenic proteins are disclosed in U.S. Pat. No. 6,949,505, the disclosures of which are hereby incorporated by reference. BMPs can be used for inducing neural cell adhesion. General methods for inducing neural cell adhesion using osteogenic proteins are disclosed in U.S. Pat. No. 6,800,603, the disclosures of which are hereby incorporated by reference. BMPs can be used for treatment and prevention of Parkinson's disease. General methods for treatment and prevention of Parkinson's disease using osteogenic proteins are disclosed in U.S. Pat. No. 6,506,729, the disclosures of which are hereby incorporated by reference.

As another example, BMPs can also be used to induce dentinogenesis. To date, the unpredictable response of dental pulp tissue to injury is a basic clinical problem in dentistry. As yet another example, BMPs can induce regenerative effects on central nervous system (CNS) repair can be assessed using a rat brain stab model.

Bioactive Co-Agents

The present invention also contemplates "bioactive co-agents" that can be co-administered with the protein preparations of the present invention include, but are not limited to, anabolic agents, anti-asthmatic agents, anti-infective agents including, for example, antiproteincterial and antimicrobial agents, anti-inflammatory agents, antimetabolite agents, antineoplastic agents, anti-bone resorption agents, anti-obesity agents, anti-pyretic and analgesic agents, anti-spasmodic agents, anti-thrombotic agents, antihistamines, biologicals, bronchodilators, cytotoxic agents, diagnostic agents, erythropoietic agents, immunomodulating agents, mineral supplements, peripheral vasodilators, stimulants, tissue growth agents, vitamins, or antigenic materials.

More particularly, the bioactive co-agents preferred for co-administration include, but are not limited to, growth factors, hormones, anti-angiogenesis factors, dextromethorphan, peptides, polypeptides, proteins, amino acids, hormones, interferons, cytokines, and vaccines. Other representative bioactive co-agents that can be co-administered include, but are not limited to, peptide drugs, protein drugs, antigens, anti-infective agents such as antibiotics, antimicrobial agents, antiviral, antiproteincterial, antiparasitic, antifungal substances and combination thereof, antiallergenics, steroidal anti-inflammatory agents, analgesics, nonsteroidal anti-inflammatory agents, and nutritional agents The bioactive co-agent may also be a substance, or metabolic precursor thereof, which is capable of promoting growth and survival of cells and tissues, or augmenting the activity of functioning cells, as for example, blood cells, neurons, muscle, bone marrow, bone cells and tissues, and the like. For example, bioactive co-agents that may be co-administered include without limitation a nerve growth promoting substance, as for example, a ganglioside, phosphatidylserine, a nerve growth factor, brain-derived neurotrophic factor. The bioactive co-agent may also be a growth factor for soft or fibrous connective tissue as, for example, a fibroblast growth factor, an epidermal growth factor, an endothelial cell growth factor, a platelet derived growth factor, an insulin-like growth factor, a periodontal ligament cell growth factor, to name but a few.

EXAMPLES

Example I

Osteoarthritis

A. Sheep Model for Prevention of Osteoarthritis

Sheep can be used as a model for osteoarthritis because it has been demonstrated that progressive osteoarthritis occurs in these animals after a single injury impact. All sheep will receive general anesthesia and using aseptic techniques, a 3 cm arthrotomy will allow access to both femorotibial joints. A spring loaded mechanical device will be used to create bilateral impact injuries to the weight bearing region of the median femoral condyle (30 Mpa, 6 mm diameter.times.2). After a routine closure of these incisions, the sheep will receive an intra-articular injection in each knee of a concentrated protein preparation of a BMP, preferably BMP-7. The sheep will be sacrificed 12 weeks postoperatively for detailed assessment (paravital staining, TUNEL staining, histopathology, cartilage, sulfated GAG analysis, biomechanical indentation testing) of the articular tissues. Histological sections will be prepared for evaluation of cartilage physiology. Sulfated glycosaminoglycan concentrations will be measured as an indicia of cartilage physiology and health. It is expected that the control group will exhibit fibrillations and erosion of the surface, whereas the BMP-treated group will show little or no sign of damage. It is expected that the BMP-treated joints will look healthier and shinier than the controls indicating regeneration and repair of the osteoarthritic lesions.

These experiments will demonstrate marked improvement, if not complete protection with BMP.

B. Guinea Pig and Rabbit Models of Osteoarthritis

The Hartley guinea pig (spontaneous) and rabbit ACL-resection (induced) osteoarthritis models will be utilized. Fourteen guinea pigs of either 3, 6 or 9 months of age will be injected in the right knee with a concentrated solution of BMP at 3-week intervals for a period of 12 weeks. The left knee will serve as an untreated control. In ten New Zealand White rabbits, the left ACL will be resected and will receive either an injection into the joint of BMP or a control solution at 3-week intervals during a 12-week evaluation period. The right knee will serve as a non ACL-resected nontreated control in all animals. All animals in both models will be evaluated for gross appearance and histologic evidence of arthritic changes using a modified Mankin scale to grade the severity of degeneration. It is expected that the BMP-7 treatment will have a profound effect in preventing degeneration in the guinea pig at the early time periods. In the rabbit ACL-resected model BMP treatment is expected to show slight improvement in the severity of degeneration in treated sites at the 12 week evaluation period. These results will demonstrate that BMP, preferably BMP-7, has some beneficial effects in preventing or slowing early stage arthritic changes.

C. Patients having a diagnosis of osteoarthritis will be treated with a protein preparation of the present invention. Certain patients will receive aqueous carrier only. In certain clinical studies, doses will be administered ranging from about 1 mg in about 100 microliters to about 30 mg in about 3 ml. In others, doses will be administered ranging from about 2 mg in about 100 microliters to about 60 mg in about 3 ml. Doses will be administered into the synovial space of various articulating joints, including but not limited to the knee and hip joints. It is expected that patients receiving at least 1 mg of a concentrated protein preparation of a BMP, preferably BMP-7, will exhibit amelioration of their symptoms. It is further expected that patients receiving at least 1 mg of concentrated protein preparation of a BMP, preferably BMP-7, will exhibit repair of joint deterioration associated with osteoarthritis.

Example II

Degenerative Disc Disease

A. Sheep Model of Disc Repair and Regeneration

Experimental induction of controlled outer annular defects in sheep initiates a sequence of events which closely reproduces, pathologically and biochemical, the evolution of disc degeneration in man. Compositional changes include an alteration in the amount of, and the types of collagens synthesized by cells of the lesion site (Kaapa et al 1994a, b, 1995 Kaapa E. et al. (1995) Collagen synthesis and types I, III, IV, and VI collagens in an animal model of disc degeneration, Spine 20, 59-67; Kaapa E et al., (1994) Collagens in the injured porcine intervertebral disc, J. Orthop. Res. 12. 93-102; and Kaapa E et al., (1994) Proteoglycan chemistry in experimentally injured porcine intervertebral disk, J. Spin. Dis. 7, 296-306) loss of large high buoyant density aggrecan type proteoglycans and an elevation in levels of the small DS substituted proteoglycans decorin and biglycan in the injured disc (Melrose J. et al, (1992) A longitudinal study of the matrix changes induced in the intervertebral disc by surgical damage to the annulus fibrosus, J Orthop Res 10:665-676; Melrose J. et al., (1997) Topographical variation in the catabolism of aggrecan in an ovine annular lesion model of experimental disc degeneration J Spinal Disord 10:55-67; and Melrose J. et al., (1997) Elevated synthesis of biglycan and decorin in an ovine annular lesion model of experimental disc degeneration, Eur Spine J 6:376-84). Changes in the vascular supply to the cartilaginous end plate (CEP) (Moore R J et al., (1992) Changes in endplate vascularity after an outer anulus tear in the sheep, Spine 17:874-878) and remodeling of vertebral bone adjacent to experimental annular defects (Moore R J, et al. (1996) Remodeling of vertebral bone after outer anular injury in sheep, Spine 21:936-940.), changes in the biomechanical competence of "repaired" lesion affected discs (Latham J M et al., (1994) Mechanical consequences of annular tears and subsequent intervertebral disc degeneration, J Clin Biomech 9:211-9), and osteoarthritic changes in spinal facet joints (Moore R J et al., (1999) Osteoarthrosis of the facet joints resulting from anular rim lesions in sheep lumbar discs, Spine, 24:519-525) as a consequence of disc degeneration have also been noted.

The Ovine Annular Lesion Model

The sheep will be fasted for 24 h prior to surgery and anesthesia will be induced with an intravenous injection of 1 g thiopentone. A lateral plain X-ray film will be taken to verify normal lumbar spine anatomy. General anesthesia will be maintained after endotracheal intubation by 2.5% halothane and monitored by pulse oximetry and end tidal $CO_2$ measurement. The left flank from the ribs to the iliac crest will be prepared for sterile surgery. The sheep will receive an intramuscular injection of 1200 mg penicillin. A skin incision will be made on the left side immediately anterior to the transverse processes of the spine and the lumbar spine will be exposed by blunt dissection using an anterior muscle-splitting technique. The vascular and neural anatomy will be respected and bleeding will be controlled by direct pressure or electrocautery as required. A total of twelve two year old sheep will receive controlled annular lesions in their L1-L2, L3-L4 and L5-L6 discs by incision through the left anterolateral annulus fibrosus parallel and adjacent to the cranial endplate using a #11 scalpel blade to create a lesion measuring 4 mm long.times.5 mm deep. The intervening lumbar discs (L2-L3, L4-L5) will not be incised. The incised discs will receive one of 3 therapies, (I) no treatment, (II) lactose solution or (III) lactose containing BMP-7. In all sheep the L3-L4 disc will receive an annular lesion with no treatment. In 4 sheep the L1-L2 discs will be treated with lactose solution only and the L5-L6 disc will be treated with lactose plus BMP-7. In the remaining 4 sheep the treatments in the L1-L2 and L5-L6 discs will be reversed to avoid any potential outcome bias associated with spinal level. A non-operated disc must remain between treated discs to allow for adequate anchorage of FSUs in subsequent mechanical testing (see below). A wire suture will be used to identify the craniad operated level for later identification purposes both in X-rays and for morphological identification. Three additional non-operated animals will also be used as controls for the biomechanical study.

Degeneration following annular incision is well established in the sheep (Osti O L et al., (1990) Volvo Award for Basic Science, Annulus tears and intervertebral disc degeneration. An experimental study using an animal model, Spine 15:762-7) and can be expected to show the earliest radiographic and histochemical evidence after 12 weeks. Three months after induction of the annular lesions the sheep will be killed by intravenous injection of 6.5 g sodium pentobarbitone and the lumbar spines will be radiographed to evaluate disc calcification, excised and processed for biomechanical (n=8) and histochemical (n=4) analyses, and, after the biomechanical testing the same discs will be zonally dissected for compositional analyses. It is expected that BMP-7 treated animals will exhibit less degeneration than untreated animals.

B. The in vivo effects of BMP-7 on the repair of intervertebral discs are studied in two rabbit models—one model involves stab-wounding of the annulus fibrosus, as described in Lipson et al., Spine 6:194 (1981), and the other model involves intradiscal C-ABC injection, as described in Kato et al., Clin. Orthop. 253:301 (1990). Briefly, for the stab-wounding method, an incision will be made in the annulus fibrosus of New Zealand White rabbits. Each rabbit will have two discs treated: one disc treated with BMP-7 and the other treated with aqueous carrier. For the intradiscal injection model, the lumbar discs of New Zealand White rabbits will be exposed and BMP-7 or aqueous carrier will be injected into the intervertebral discs. At varying times following treatment, the rabbits will be euthanized and the effects of BMP-7 on the repair of the intervertebral disc space will be evaluated by methods well known in the art. These methods include magnetic resonance imaging, mechanical tests, histological analysis, and biochemical studies of the various extracellular matrix components in the repaired discs. It is expected that BMP-7 treated animals will exhibit improved disc health and less degeneration than untreated animals.

C. Patients having a diagnosis of degenerative disc disease will be treated with a protein preparation of the present invention.

It is expected that administration of the protein preparations of the present invention to patients presenting with lower back pain, particularly discogenic pain diagnosed using a discogram, will result in amelioration of such pain. In a preferred treatment modality, such patients will receive at least one intradiscal injection of a protein preparation of the present invention. Such patients will display amelioration of pain as compared to other patients who are not treated with a protein preparation of the present invention. It is expected that BMP-7 treatment will be particularly effective for such patients.

Example III

Non-Skeletal Tissue Repair

It is expected that administration of the protein preparations of the present invention to patients having disorders, injuries or diseases of non-skeletal tissue will result in amelioration and/or repair of such disorders, injuries or diseases. As explained elsewhere herein, protein preparations containing certain preferred morphogenic proteins will be useful for repair of soft tissues such as but not limited to kidney and liver, and will be useful for treatment of opthamologic and neural defects to name but a few. It is expected that administration via a systemic route or via local administration will result in improvements relative to untreated subjects.

Example IV

Prophylactic Administration Post-Injury

It is expected that certain disorders, injuries or diseases will benefit from treatment with the protein preparations of the present invention prior to surgical intervention. Prophylactic administration is expected to facilitate the likelihood of post-surgical healing and to promote restoration of a normal or near-normal physiology. For example, in the case of a patient suffering from DDD, it is expected that treatment with a concentrated preparation of a BMP, preferably BMP-7, prior to surgery will be beneficial. In certain patients, multiple pre-surgical treatments will be beneficial. Patients treated prior to surgery will receive a treatment concurrent with surgery. Certain other patients will benefit from multiple treatments post-surgery. In each of the foregoing situations, it is expected that treated patients will exhibit better disc health than untreated patients.

Example V

Preparation of BMP-7 at Certain High Concentrations (20 to 40 mg/mL) in Certain Preferred Aqueous Carriers The following exemplary method increases ease of protein processing during manufacturing, while reducing in-process product losses and yielding the final desired high concentration protein preparation of the present invention.

This Example outlines a method for processing (preparation, fill, lyophilization, and finish operations) BMP-7 at low concentrations ($\leq$20 mg/mL), while yielding a product that can be reconstituted to a desired target higher protein concentration (20 to 40 mg/mL). This methodology allows execution of all manufacturing operations at a lower protein concentration—this increases ease of processing as the viscosity of the solution handled is lower and it also reduces in-process losses during manufacturing (since a fixed volume lost contains a lower mass of protein due to the lower concentration used during processing). The lower concentration used during processing also allows for the product to be stored and processed at refrigerated temperatures (2 to 8° C.), without resulting in a dramatic increase in viscosity as would otherwise be observed if high protein concentrations were used during processing.

Usually drug products are processed and filled at the same concentration as the final desired target. For example, if the target protein concentration for administration is 40 mg/mL, the protein preparation (in the presence of appropriate stabilizing excipients) would typically be filled at 40 mg/mL and the freeze-dried product reconstituted with the same volume of diluent as the fill volume prior to lyophilization (freeze-drying).

In the methodology disclosed in this document, a different approach is used. For example, if it is desired to have 1 mL of protein solution at 40 mg/mL for administration, the processing (upstream manufacturing) would be conducted at a lower concentration, say 20 mg/mL. The fill would be 2 mL at 20 mg/mL, and the product would be reconstituted with 1 mL reconstitution diluent following freeze-drying. Hence, the manufacturing (processing) operations are conducted at a lower concentration than the final target yielding the following benefits: (a) this increases ease of processing as the viscosity of the solution handled is lower, (b) it also reduces in-process losses during manufacturing (since a fixed volume lost contains a lower mass of protein due to the lower concentration used during processing), (c) the lower concentration used during processing also allows for the in-process intermediates to be stored (and/or processed) at refrigerated temperatures (2 to 8° C.), without resulting in a dramatic increase in viscosity as would otherwise be observed if high protein concentrations were used during processing (See FIG. 1).

Likewise, in the same spirit of the invention disclosure, if a target volume of V mL is desired at a protein concentration of C mg/mL for administration, the protein preparation/fill/finish operations can be conducted at C/N mg/mL with a fill volume of V*N mg/mL, with final reconstitution of the lyophilized product with V mL water, where N (N>1) is a suitable scaling factor, which can be appropriately chosen based on the viscosity and processability of the protein solution.

This methodology allows execution of all manufacturing operations at a lower protein concentration—this increases ease of processing as the viscosity of the solution handled is lower and it also reduces in-process losses during manufacturing (since a fixed volume lost contains a lower mass of protein due to the lower concentration used during processing). The lower concentration used during processing also allows for the product to be stored and processed at refrigerated temperatures (2 to 8° C.), without resulting in a dramatic increase in viscosity as would otherwise be observed if high protein concentrations were used during processing.

In addition, the above advantages also serve to yield a product with better quality attributes (for example, if processing is done at a lower protein concentration then critical physicochemical protein attributes such as aggregation tend to be lower than if the protein was processed at a higher concentration) and lower cost of goods (lower COGS due to smaller mass loss of protein and a higher quality product, as discussed above).

The above-described protocol has been successfully implemented to manufacture protein preparations ranging from about 10 to about 60 mg/ml. Using a titration matrix of varying ionic strengths, pHs and protein concentrations (mg/ml), it was discovered that highly concentrated preparations of protein in aqueous carriers are possible without risk of precipitation. Generally, as ionic strength is increased, pH is decreased thereby maintaining a solubilized protein in an aqueous carrier comprising one or more of the buffer systems described elsewhere herein. Stabilizing excipients can be used as described earlier.

Example VI 30 mg/mL BMP-7 in 5% Trehalose with 0.75 mL Volume Post-Reconstitution Bulk BMP-7 was obtained as a starting material at 2 mg/mL in 50 mM acetic acid (pH=3.0). Tangential flow filtration (or cross-flow filtration) was performed for protein concentration and buffer exchange. Buffer exchange was performed against 10 mM lactate buffer (pH=3.0) and 10× (i.e., about 10-fold) difiltration volume exchanges were performed to achieve a >99.9% buffer exchange efficiency. Trehalose (2.5% w/v) may be added either during diafiltration or following diafiltration. In this Example, trehalose was added following ultrafiltration and diafiltration (UF/DF). Protein concentration was adjusted to 15 mg/mL in 10 mM lactate buffer+2.5% w/v trehalose. Thereafter, 1.5 mL of solution was filled into each 3 mL vial and lyophilized. Post-lyophilization (or freeze-drying), a pharmaceutically elegant cake was obtained as the protein preparation which was reconstituted with 0.75 mg water-for-injection (WFI). This yielded a 30 mg/mL BMP-7 solution in 5% trehalose. The resulting product had desirable product quality attributes suitable for intended clinical uses, such as but not limited to, levels of aggregation and oxidation within accepted limits.

EQUIVALENTS

The invention may be embodied in other specific forms without departing from the spirit or essential characteristics thereof. The present embodiments are therefore to be considered illustrative and not restrictive, the scope of the invention being indicated by the appended claims rather than by the foregoing description, and all changes which come within the meaning and range of equivalency of the claims are therefore intended to be embraced therein.

We claim:

1. A preparation of bone morphogenetic protein comprising:
    an aqueous carrier having an ionic strength of about 20-40 mM; and
    a bone morphogenetic protein solubilized in said carrier at a concentration of 20-40 mg/ml.

2. The protein preparation of claim 1, wherein the carrier has a pH of about 2.5-4.

3. The protein preparation of claim 2, wherein the bone morphogenetic protein is BMP-7; and wherein the aqueous carrier has an ionic strength of about 10 mM and a pH of about 3.5.

4. The protein preparation of claim 2, wherein the preparation is solubilized at a temperature of about 4° C. to about 25° C.

5. The protein preparation of claim 1, further comprising a stabilizing excipient selected from the group consisting of: sugars, polyols, surfactants, and any combination thereof.

6. The protein preparation of claim 1, wherein the aqueous carrier comprises a buffer of the single acidic group type selected from the group consisting of: potassium phosphate, proprionic acid, lactic acid, trifloroacetic acid and acetic acid; or a buffer of the two acidic group type selected from the group consisting of: sodium glutamate and sodium succinate.

7. The protein preparation of claim 1, wherein the preparation is lyophilized or a reconstituted lyophilate.

8. The protein preparation of claim 1, wherein the protein is a member of the BMP subfamily of the TGF-beta superfamily of proteins selected from the group consisting of BMP-2, BMP-4, BMP-5, BMP-6, BMP-7, GDF-5, GDF-6, GDF-7, and sequence variants of any one of the foregoing.

9. The protein preparation of claim 8, wherein the protein is BMP-7.

10. A kit for the treatment of a disorder, injury or disease comprising a lyophilized bone morphogenetic protein and a reconstitution diluent, wherein the protein and the diluent are in separate containers, and further wherein the kit comprises a plurality of separate containers each containing an amount of diluent, such that the amounts of diluent are sufficient to prepare solubilized protein preparations ranging in concentration from 20 mg/ml to 40 mg/ml and wherein the diluent is a carrier having a concentration of about 20-40 mM for use in the treatment of a disorder, injury or disease.

* * * * *